United States Patent
Nord et al.

(10) Patent No.: US 12,036,422 B2
(45) Date of Patent: Jul. 16, 2024

(54) EXPANSION OF SEARCH SPACE FOR MULTICRITERIA OPTIMIZATION IN RADIATION TREATMENT PLANNING

(71) Applicant: Varian Medical Systems International AG, Steinhausen (CH)

(72) Inventors: Janne Nord, Espoo (FI); Esa Kuusela, Espoo (FI); Perttu Niemelä, Espoo (FI); Tuomas Tallinen, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 1283 days.

(21) Appl. No.: 16/680,362

(22) Filed: Nov. 11, 2019

(65) Prior Publication Data

US 2021/0138267 A1    May 13, 2021

(51) Int. Cl.
*A61N 5/10*    (2006.01)

(52) U.S. Cl.
CPC ......... *A61N 5/1038* (2013.01); *A61N 5/1031* (2013.01); *A61N 5/1047* (2013.01); *A61N 2005/1041* (2013.01); *A61N 2005/1074* (2013.01)

(58) Field of Classification Search
CPC .. A61N 5/1031; A61N 5/1036; A61N 5/1038; A61N 5/1045; A61N 5/1047; A61N 2005/1041; A61N 2005/1074
See application file for complete search history.

(56) References Cited

U.S. PATENT DOCUMENTS

| | | | |
|---|---|---|---|
| 10,661,097 B2 | 5/2020 | Tallinen et al. | |
| 2012/0045035 A1 | 2/2012 | Nord et al. | |
| 2013/0197878 A1* | 8/2013 | Fiege | G06F 30/20 703/2 |
| 2013/0304503 A1* | 11/2013 | Kuefer | A61N 5/1031 705/2 |
| 2018/0021594 A1 | 1/2018 | Papp et al. | |
| 2018/0185669 A1* | 7/2018 | Kuusela | G21K 1/025 |
| 2018/0221685 A1* | 8/2018 | Eriksson | G16H 50/20 |

FOREIGN PATENT DOCUMENTS

WO    2011153639    12/2011

OTHER PUBLICATIONS

U.S. Appl. No. 15/711,516, Corrected Notice of Allowability dated Apr. 13, 2020, 3 pages.

(Continued)

*Primary Examiner* — Carrie R Dorna
(74) *Attorney, Agent, or Firm* — Fitch, Even, Tabin & Flannery LLP

(57) ABSTRACT

A search space used for multicriteria optimization in radiation treatment planning can be expanded using extrapolation. For instance, given an initial set of base plans, one or more virtual plans can be generated by assigning a weight to each base plan such that at least one of the weights is less than zero and/or such that the sum of the weights is not normalized to 1. The dose distribution for the virtual plan is computed as the weighted sum of the dose distributions of the base plans. Virtual plans criteria can be used together with the initial set of base plans to define an expanded search space within which interpolation can be performed to identify an optimal treatment plan.

16 Claims, 10 Drawing Sheets

(56) References Cited

OTHER PUBLICATIONS

U.S. Appl. No. 15/711,516, Non-Final Office Action dated Sep. 19, 2019, 7 pages.
U.S. Appl. No. 15/711,516, Notice of Allowance dated Jan. 16, 2020, 5 pages.
Chen et al., Multi Criteria Optimization Informed VMAT Planning, Medical Dosimetry, vol. 39, No. 1, 2014, pp. 64-73.
European Application No. 18194766.4, Extended European Search Report dated Feb. 18, 2019, 6 pages.
European Application No. EP18194766.4, "Office Action", dated Feb. 19, 2020, 4 pages.
Monz et al., "Pareto Navigation-Algorithmic Foundation of Interactive Multi-Criteria IMRT Planning", Physics in Medicine and Biology, vol. 53, No. 4, Feb. 21, 2008, pp. 985-998.

* cited by examiner

EXPANSION OF SEARCH SPACE FOR MULTICRITERIA OPTIMIZATION IN RADIATION TREATMENT PLANNING

BACKGROUND

The present disclosure relates generally to treatment planning for radiation therapy and more specifically to techniques for expanding a search space for multicriteria optimization in radiation treatment planning.

In general, radiation therapy consists of the use of ionizing radiation to treat living tissue, usually tumors. Many different types of ionizing radiation are used in radiation therapy, including high-energy x-rays, electron beams, and proton beams. The process of administering radiation therapy to a patient can be similar across different types of radiation. Typically, an external-beam radiation treatment system is used. Such systems provide a linear accelerator that produces a beam of the desired type at a beam source and collimators including a multileaf collimator (MLC) to shape the beam that emerges from the beam source. The beam delivery system (including the beam source and collimators) is generally mounted on a movable gantry that can be moved around a treatment couch on which a patient is placed, allowing the radiation beam to be delivered from different angles relative to the patient.

Systems of this kind are used for various treatment options. One option is intensity-modulated radiotherapy (IMRT), in which the beam source is positioned at a desired angle, and the MLC is modulated to control the dose received by different tissues. During a treatment session, the beam source and/or the MLC may be repositioned, allowing radiation to be delivered from different angles. In IMRT, the beam source remains stationary while radiation is being delivered. Another treatment option is volumetric modulated arc therapy (VMAT), in which the beam source traverses an arc around the patient while delivering radiation. In both IMRT and VMAT, the overarching goal is to deliver a therapeutically effective dose of radiation (typically a high and uniform dose) to a target volume (typically a tumor) within the patient's body while minimizing the dose delivered to surrounding tissues (in particular, healthy organs or tissues that may be located close to the target volume).

Effective radiation therapy requires treatment planning to determine machine parameters that will optimally achieve the overarching goal. In the case of IMRT, a treatment plan may specify machine parameters such as positions of the beam source and collimators (including MLC leaf settings), beam intensity (e.g., dose rate), and duration of exposure (also referred to as "beam-on time"); the plan may include multiple control points, each defined by a set of machine parameters. In the case of VMAT, a treatment plan may specify all of the same machine parameters as in IMRT, plus additional parameters defining an arc to be traversed and in some instances speed of traversing the arc. During treatment, a treatment plan can be used to control operation of the radiotherapy system, and operating the radiotherapy system according to the treatment plan results in delivering a desired dose distribution to the patient.

Treatment planning is usually approached via the "inverse" problem of determining the optimal combination of machine parameters—such as beam intensity, beam shaping, beam direction(s), exposure duration—to deliver a desired total radiation dose to the target volume (or multiple target volumes) while minimizing the dose delivered to nearby organs or tissues (often referred to as "organs at risk," or "OAR"). The desired radiation doses can be expressed as a set of treatment objectives (or clinical goals), and a cost function can be defined to quantify a difference between a predicted radiation dose and the set of treatment objectives. This cost function allows a practitioner to compare different treatment options.

SUMMARY

Among the challenges of treatment planning is providing a search space that reflects the full capabilities of the radiation treatment system. In some treatment planning systems, a search space is defined by generating a set of "base plans," where each base plan corresponds to a different set of machine parameter values and where a dose distribution is modeled for each of the base plans. The base plans can be selected, e.g., by identifying a set of plans that are Pareto-optimized with respect to different clinical goals (or treatment objectives). Navigation of the search space is facilitated by interpolating among the dose distributions of different base plans to predict a dose distribution for an interpolated plan, which can assist a user (e.g., a clinician) in selecting an optimal dose distribution relative to the clinical goals. If the set of base plans is not reflective of the full range of capabilities of the radiation treatment system, an interpolation-based search may not lead to the best possible treatment plan that a given radiation treatment system can deliver.

Accordingly, some embodiments of the present invention relate to expanding the search space used for multicriteria optimization. For instance, given a set of base plans, one or more additional "virtual" plans can be generated by extrapolating from the set of base plans. In some embodiments, a virtual plan can be generated by assigning a weight to each base plan such that at least one of the weights is less than zero and/or such that the sum of the weights is not normalized to 1. (This differs from interpolation, where all weights are positive and the weights are normalized such that the sum of weights is equal to 1.) The dose distribution for the virtual plan is computed as the weighted sum of the dose distributions of the base plans. In some embodiments, a virtual plan can be screened according to various criteria, such as whether the virtual plan is physically plausible (e.g., a virtual plan that includes large negative doses and/or negative doses over extended regions may be physically implausible), whether the virtual plan is implausibly good (e.g., a virtual plan that is better with respect to satisfying all clinical goals than any of the base plans may be considered implausibly good), or whether the virtual plan is clearly sub-optimal (e.g., a virtual plan that is worse with respect to satisfying all clinical goals than all of the base plans may be considered sub-optimal). Virtual plans that satisfy any applicable screening criteria can be used together with the base plans to define an expanded search space for user exploration (also referred to as navigation). User exploration can proceed based on interpolation among the base plans and virtual plans that define the expanded search space.

The following detailed description, together with the accompanying drawings, will provide a better understanding of the nature and advantages of the claimed invention.

DEFINITIONS

Figure 1:
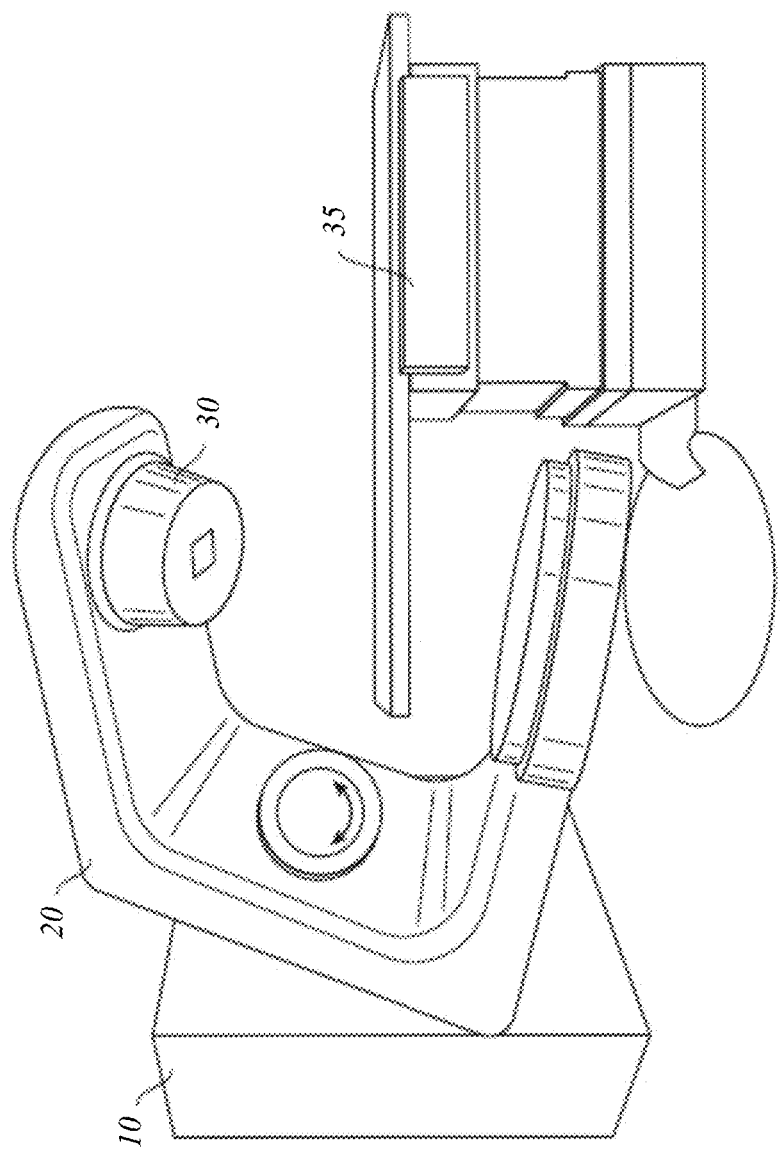
FIG. 1 shows a perspective view of radiation treatment system suitable for use in some embodiments of the present invention.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" refer to tissue intended to receive a therapeutic prescribed dose. The irradiated volume is generally larger than the target volume and may include organs or tissues that are not intended to receive a therapeutic dose. Such organs or tissues are sometimes referred to as "organs at risk" (OAR).

A "dose distribution" provides information about the variation in the dose of radiation with position. A dose distribution can be represented in many formats, e.g., a dose volume histogram (DVH) or a dose matrix. A DVH can summarize three-dimensional (3D) dose distributions in a graphical format, e.g., where the horizontal axis is the dose (e.g., in units of grays (Gy)) absorbed by a particular volume or structure (which can be the target volume, an OAR, or any other well-defined volume) and the vertical axis is a volumetric percentage. In a differential DVH, the height of a bar at a particular dose indicates the volumetric percentage of the volume in question that receives the particular dose. In a cumulative DVH, the height of a bar at a particular dose represents the volumetric percentage of the volume in question that receives greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can show the dose that each part of the body receives; for instance, the three-dimensional treatment volume can be segmented into voxels, and the dose matrix can identify a dose received (or predicted) for each voxel.

A "dose prediction model" receives patient data and machine parameters and outputs a dose distribution that is predicted to be obtained. The output of a dose prediction model can include, e.g., a DVH or a dose matrix from which a DVH can be computed. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test radiation treatment plans whose dose distribution has been determined via other means (e.g., by optimizing a cost function). For example, the accuracy can be determined based on how well the model predicts the actual dose distributions obtained by optimizing a cost function. Examples of techniques for creating and selecting a dose prediction model for a treatment plan are described in U.S. Pat. No. 9,827,445, issued Nov. 28, 2017.

A "radiation treatment plan" (also referred to as a "treatment plan" or "plan") can include a particular dose distribution or set of radiation fields that provides a particular dose distribution, machine parameters for achieving the dose distribution for a given patient, and information about the given patient. Examples of radiation treatment plans and generation thereof are described in U.S. Pat. No. 7,796,731, issued Sep. 14, 2010; U.S. Pat. No. 7,801,270, issued Sep. 21, 2010; U.S. Pat. No. 9,827,445, issued Nov. 28, 2017; and U.S. Pat. No. 10,166,406, issued Jan. 1, 2019.

"Monitor unit" (MU) is a measure of machine output from a clinical accelerator for radiation therapy such as a linear accelerator. Monitor units are measured by monitor chambers, which are ionization chambers that measure the dose delivered by a beam and are built into the treatment head of radiotherapy linear accelerators. Linear accelerators are calibrated to give a particular absorbed dose under particular conditions, although the definition and measurement configuration will vary between centers.

Two common definitions of monitor units are: (1) the monitor chamber reads 100 MU when an absorbed dose of 1 gray (100 rads) is delivered in the centerline of the field to a point at the depth of maximum dose in a water-equivalent phantom whose surface is at the isocenter of the machine (e.g., at 100 cm from the source for a typical machine) with a field size at the surface of 10 cm×10 cm; and (2) the monitor chamber reads 100 MU when an absorbed dose of 1 Gy (100 rad) is delivered to a point at a given depth in the phantom with the surface of the phantom positioned so that the specified point is at the isocenter of the machine and the field size is 10 cm×10 cm at the isocenter.

Some linear accelerators are calibrated using source-to-axis distance (SAD) instead of source-to-surface distance (SSD), and calibration (monitor unit definition) may vary depending on hospital custom. Early radiotherapy was performed using "constant SSD" treatments, and so the definition of monitor unit was adopted to reflect this calibration geometry. Modern radiotherapy is performed using isocentric radiation treatment plans, so newer definitions of the monitor unit are based on geometry at the isocenter based on the source-to-axis distance (SAD).

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, the gantry angle, the collimator angle, and the position of each MLC leaf. The term "control point" refers to a parametrical point of a radiation treatment field that includes spatial information about the treatment axes and may also specify collimator settings, beam intensity or dose rate (e.g., using MU count and/or the related concept of the meterset weight), and/or speed of motion of the beam source (including a speed of a movable gantry supporting the beam source).

DETAILED DESCRIPTION

1. Radiation Therapy Systems

External beam therapy (EBT), also called external radiation therapy, is a method for delivering a beam or several beams of photons (e.g., x-rays) or other particles (e.g., protons, electrons) to a patient's tumor or other target within or on the surface of a patient. Beams are generated outside the patient and are targeted at the tumor site.

Figure 2:
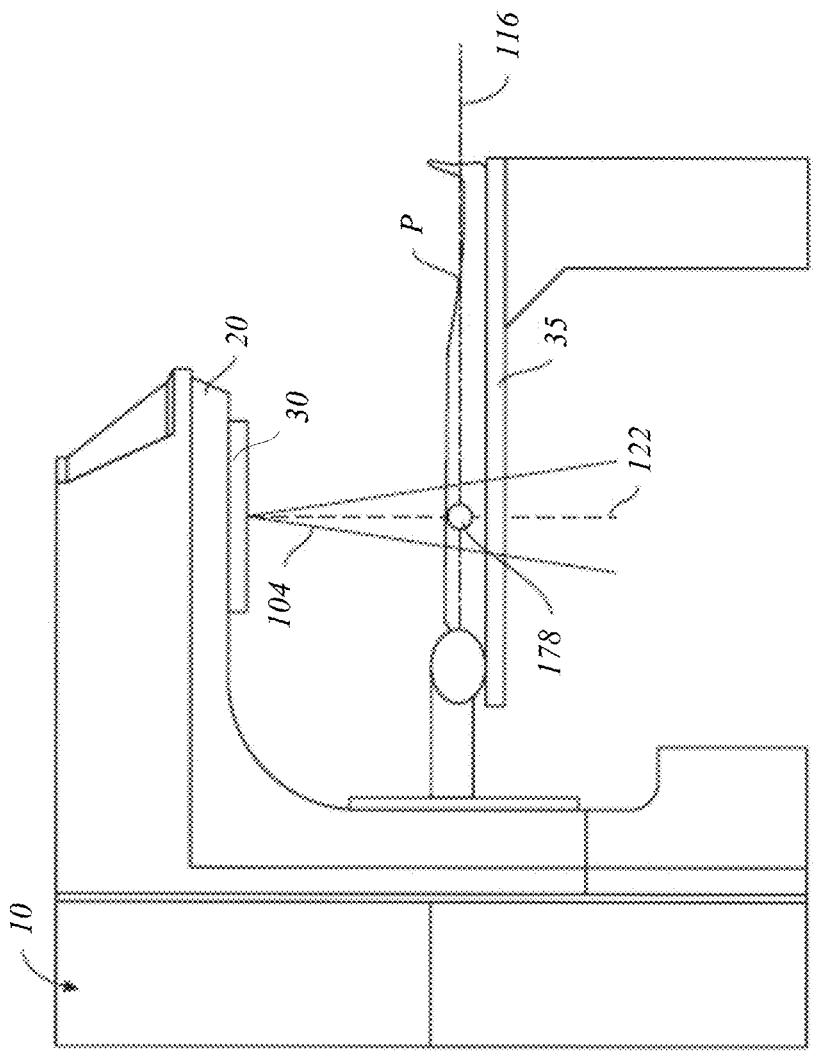
FIG. 2 shows a somewhat more detailed side view of the radiation treatment system of FIG. 1.

FIGS. 1 and 2 depict a radiation treatment system 100 that may be used in connection with an embodiment of the present invention. FIG. 1 shows a perspective view of radiation treatment system 100 (in this case incorporating a linear accelerator). Radiation treatment system 100 may be capable of generating either a particle beam (e.g., electrons or protons) or a photon beam (e.g., x-rays) for use in the radiotherapy treatment of a patient on a treatment couch 35. For purposes of the present description, x-ray irradiation will be assumed. However, it will be appreciated by those skilled in the art that the same principles apply to other systems, including electron beam systems and heavy-ion (e.g., proton) beam systems.

Stand 10 supports a rotatable gantry 20 with a treatment head 30. Next to stand 10 there is arranged a control unit (not shown) which includes control circuitry for controlling the different modes of operation of radiation treatment system 100. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

FIG. 2 shows a somewhat more detailed side view of radiation treatment system 100. A patient P is shown lying on treatment couch 35. X-rays formed as described above are emitted from the metal target in treatment head 30 in a divergent beam 104. Typically, a patient plane 116, which is perpendicular to the page in FIG. 2, is positioned about one meter from the x-ray source (e.g., the metal target), and the axis of gantry 20 is located in patient plane 116, such that the distance between the target in treatment head 30 and isocenter 178 remains constant when gantry 20 is rotated. Isocenter 178 is a point located at the intersection between patient plane 116 and the central axis of beam 122. Patient P can be positioned on treatment couch 35 such that a treatment volume to be irradiated is located about isocenter 178.

Figure 3:
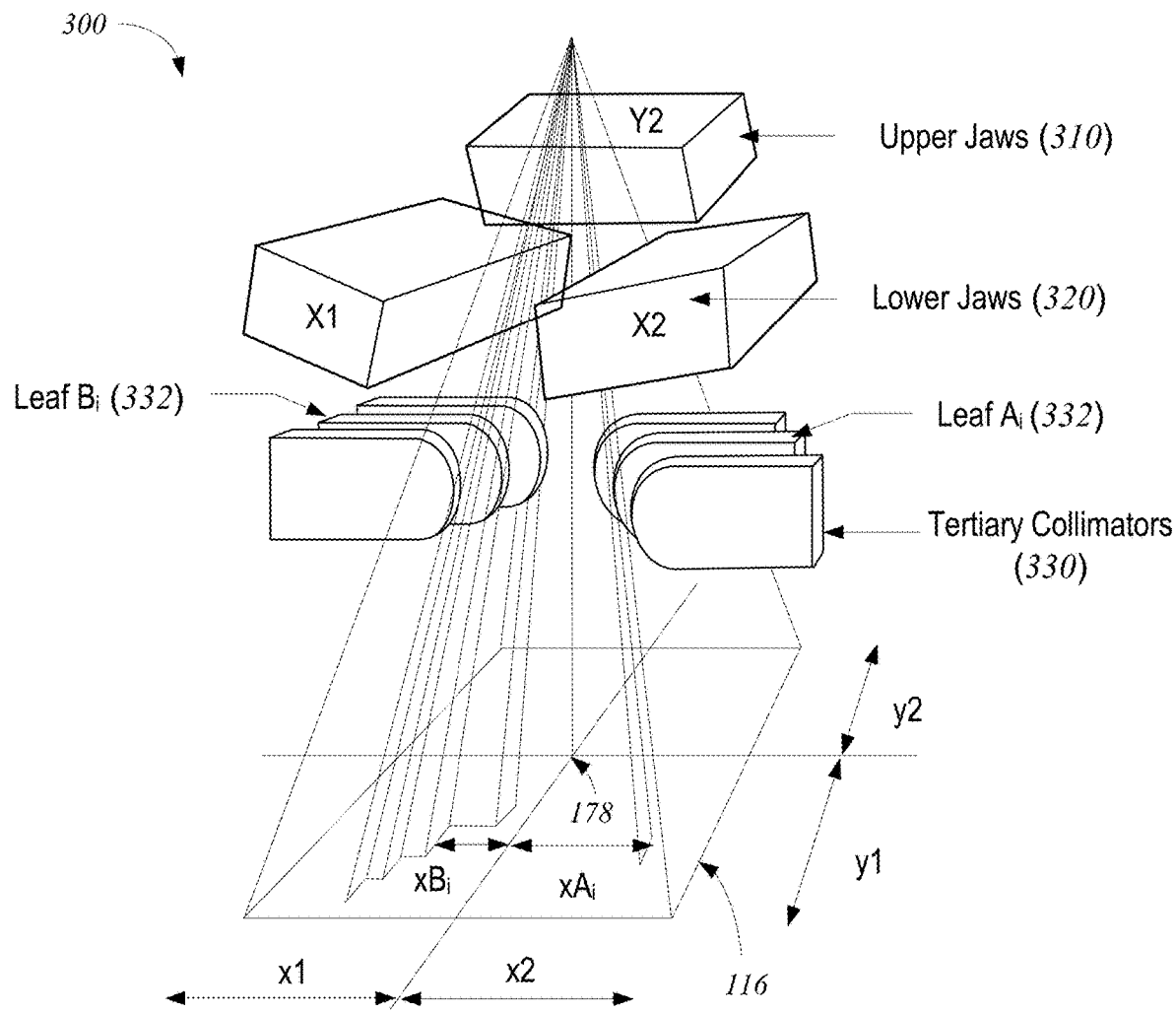
FIG. 3 shows schematically a photon collimation system that can be used in the radiation treatment system of FIGS. 1 and 2.

In some embodiments, the beam can be shaped, e.g., using configurable collimators, to optimize the dose distribution to selectively target a tumor or other diseased tissue. FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in patient plane 116 and the location of isocenter 178 are indicated. Upper jaws 310, lower jaws 320, and leaves 332 of MLC 330 are made at least partially of an x-ray blocking material and are positioned in treatment head 30 (shown in FIG. 2) to define the width of the x-ray beam at patient plane 116. Typically, jaws 310 and 320 are moveable and, when fully open, define a maximum beam width of about 40 cm×40 cm at patient plane 116. MLC 330 is positioned at the exit of treatment head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
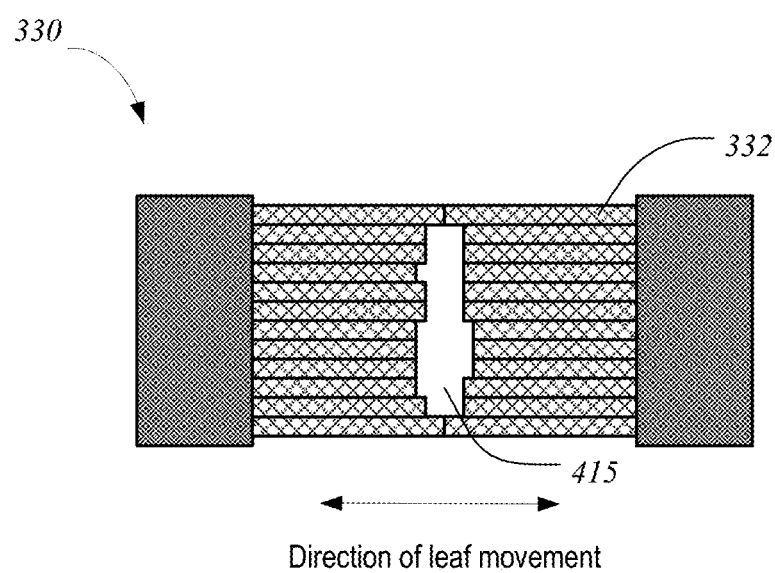
FIG. 4 shows an exemplary MLC plane that can be used in the photon collimation system of FIG. 3.

FIG. 4 shows an exemplary MLC plane having a plurality of leaves 332, arranged in opposing pairs, and an aperture 415 created by selected leaf movements. Radiation passes through and is shaped by aperture 415. Thus, MLC 330 can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to isocenter 178 in the treatment path of the x-ray beam, is defined by jaws 310 and 320, the leaf sequence of MLC 330, and the collimator angle, i.e., the angle at which MLC 330 sits in treatment head 30. In some embodiments, the position of jaws 310 and 320, the leaf sequence of MLC 330, and the collimator angle are all controllable machine parameters; in other embodiments, some of these parameters may be fixed. Examples of an MLC and leaf sequence optimization are described in U.S. Pat. No. 7,796,731, issued Sep. 14, 2010.

Figure 5:
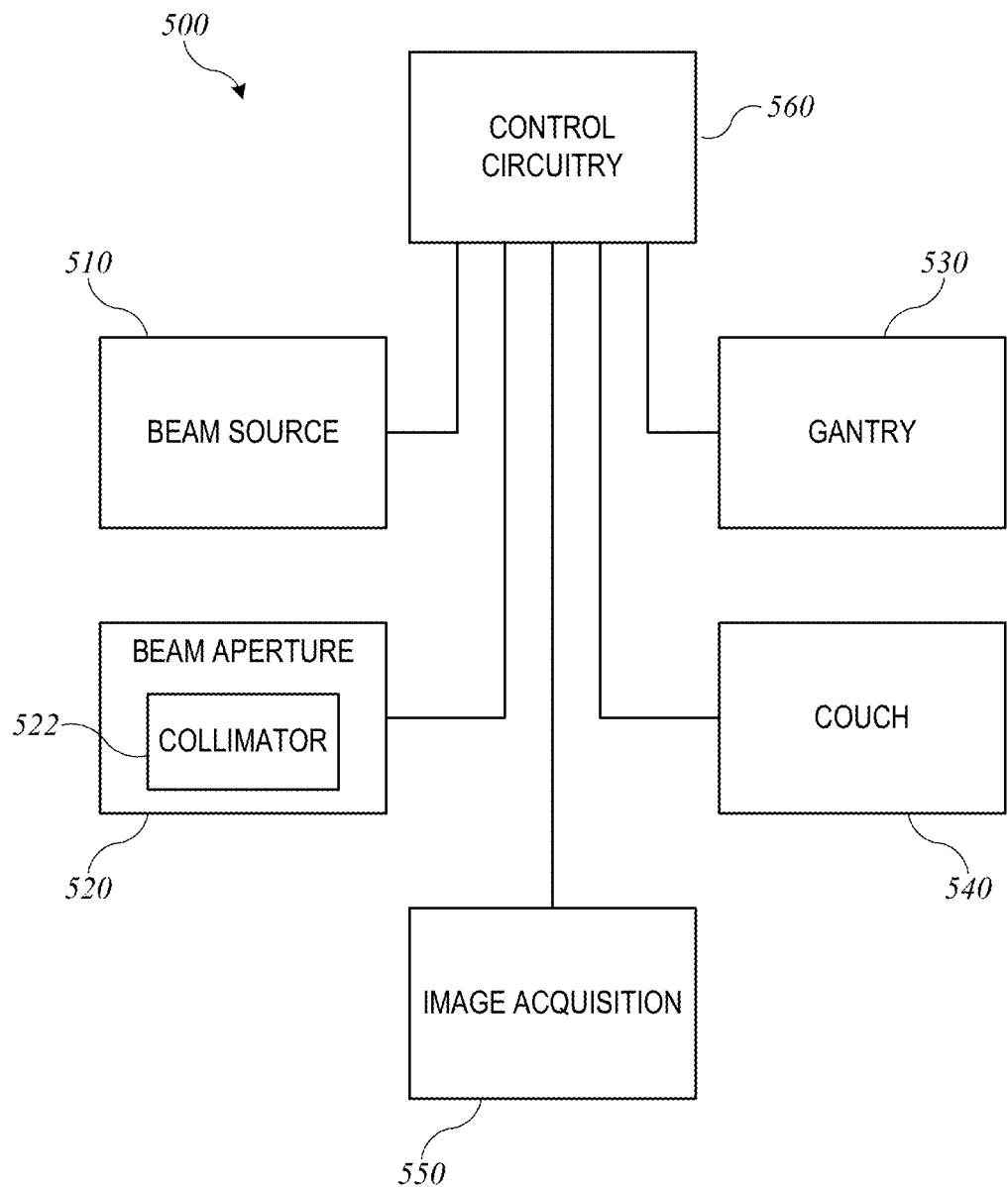
FIG. 5 shows a block diagram of an external-beam radiation treatment system implementing radiation treatment system 100 of FIGS. 1 and 2.

FIG. 5 shows a block diagram of an external-beam radiation treatment system 500 implementing radiation treatment system 100 of FIGS. 1 and 2. Radiation treatment system 500 includes a beam source 510, a beam aperture 520, a gantry 530, and a couch 540. Beam source 510 is configured to generate a beam of therapeutic radiation. This beam of radiation may include x-rays, particles, or the like. Beam aperture 520 includes an adjustable multi-leaf collimator (MLC) 522, which can be an implementation of MLC 330 described above, for spatially filtering the radiation beam. Couch 540, which can be an implementation of treatment couch 35 of FIGS. 1 and 2, is configured to support and position a patient during treatment. Couch 540 may have six degrees of freedom (the translational offsets X, Y, and Z, and the rotation, pitch, and yaw), which may be treated as machine parameters.

Gantry 530, which can be an implementation of gantry 20, houses beam source 510 and beam aperture 520. Gantry 530 can be movable, e.g., rotatable, around a fixed axis, and volumetric modulated arc therapy ("VMAT") treatment can be performed by rotating gantry 530 while beam source 510 is delivering beam. The arc to be traversed (e.g., starting and ending points) and/or speed of traversal can be treated as additional machine parameters.

In some embodiments, beam source 510 can be configured to generate imaging radiation as well as therapeutic radiation. Accordingly, radiation treatment system 500 may also include an image acquisition system 550 that comprises one or more imaging detectors mounted to gantry 530 (e.g., on an arm opposite beam aperture 520).

Radiation treatment system 500 further includes control circuitry 560 for controlling the operation of beam source 510, beam aperture 520, gantry 530, couch 540, and image acquisition system 550. Control circuitry 560 may include hardware, software, and memory for controlling the operation of these various components of radiation treatment system 500. Control circuitry 560 can comprise a fixed-purpose hard-wired platform or can comprise a partially or wholly-programmable platform. Control circuitry 560 can be configured to carry out various steps, actions, and other functions described herein. In some embodiments, control circuitry 560 may include a memory for receiving and storing a radiation treatment plan that defines the spatial points or control points of one or more treatment fields. Control circuitry 560 may then send control signals to the various components of radiation treatment system 500, such as beam source 510, beam aperture 520, gantry 530, and couch 540, to execute the radiation treatment plan. In some embodiments, control circuitry 560 may include an optimization engine to determine a radiation treatment plan; in other embodiments, an optimization engine can be provided in a separate computer system that delivers a radiation treatment plan to control circuitry 560 via a network interface or computer-readable storage medium.

2. Treatment Planning Overview

For therapeutically effective use of radiation treatment system 100 (or similar systems), it is generally desirable to develop a treatment plan prior to exposing a patient to radiation. During treatment planning, a medical practitioner or other user of a treatment planning system or method identifies a set of clinical goals (also referred to as treatment objectives) specifying desired upper or lower limits on the radiation dose to be delivered to various regions of interest within the irradiation volume. The regions of interest generally include one or more target structures (which can include tumors or other tissue to be treated) and one or more organs at risk (OAR) (which can include any healthy tissues or structures that may be near enough to a target structure to be subjected to at least some radiation). By way of example, if the target structure is a prostate tumor, associated OAR may include the bladder, spinal cord, and rectum. For a target structure, a clinical goal is generally defined as a uniform and therapeutically effective ("high") dose across the entire structure. For an OAR, a clinical goal is generally defined with reference to an upper limit on the dose, with the goal of avoiding or minimizing radiation damage to healthy tissue; the particular upper limit generally depends on the tissue type. Treatment planning involves identifying a set of treatment fields (and corresponding machine parameter settings to produce the fields) that satisfy the clinical goals. Depending on implementation, the treatment fields may include stationary treatment fields (where the direction and distance to the treatment target is fixed during beam-on) and/or dynamic treatment fields (where the direction of incidence to the treatment target changes during continuous irradiation).

In practice, the clinical goals may conflict with each other, in the sense that not all of the clinical goals can be satisfied by any particular treatment plan (i.e., set of treatment fields). Where clinical goals conflict, interactive multicriteria optimization (MCO) can be used to find a treatment plan with clinically acceptable tradeoffs.

To support MCO, a "search space" of treatment plans can be defined by generating a set of "base" plans. For instance, a dose prediction model can be used to predict outcomes (e.g., dose distributions) for various combinations of adjustable machine parameters (e.g., beam intensity, beam aperture, MLC leaf sequence, duration of exposure, relative position of beam and patient), and the cost function can be computed for various alternative outcomes. In some embodiments, an initial set of base plans is selected by identifying plans that define a Pareto-optimal surface in a space of quality metrics for treatment plans. The quality metrics for a treatment plan can be defined with reference to the clinical goals. In examples described herein, it is assumed that each quality metric is defined based on the difference between the clinical goal and the (predicted) outcome of a treatment plan, and the definitions are such that the quality metric is always nonnegative and values closer to zero indicate closer match to the clinical goal. Those skilled in the art will appreciate that other definitions of quality metrics can be used, including definitions where higher values of a quality metric indicate closer match to the clinical goal. As used herein, a particular treatment plan is Pareto-optimal with respect to the clinical goals if the plan is such that the performance relative to any one of the clinical goals cannot be improved without decreasing performance relative to a different clinical goal. Examples of techniques for generating a set of Pareto-optimal plans for a given set of clinical goals are known in the art (see, e.g., U.S. Patent Application Publication No. 2019/0083814, published Mar. 21, 2019), and detailed description of such techniques is omitted as not being critical to understanding the present disclosure. As described below, in some embodiments of the present invention, an initial search space (e.g., a search space defined by a set of Pareto-optimal plans) can be expanded by extrapolating from the outcomes of the base plans to generate outcomes for one or more "virtual" plans.

To generate a base plan for MCO, a cost function that includes cost contributions related to quality metrics (corresponding to different clinical goals) can be formulated. To generate multiple base plans, the cost function can be varied so that so that different base plans emphasize different clinical goals. A cost function can be defined, e.g., as a weighted sum of the quality metrics, and an optimized solution (in this case, a base plan) can be found by minimization of the cost function. A minimum value of the cost function can be found, e.g., using a gradient descent method. For example, the cost function gradient can be used to identify a direction of steepest descent; a fixed step size can be followed in that direction; and the cost function can be recomputed at the new location. This process can be iterated until convergence (e.g., defined as minimal change in the cost function over some number of iterations). Other techniques, such as a conjugate gradient, Newton or quasi-Newton method can be used to determine the search direction for an iteration.

In MCO, outcomes of treatment plans other than the base plans and the virtual plans can be approximated by interpolating the radiation doses between different base plans and/or virtual plans, together with the constraint that the interpolated plan is Pareto-optimal within the clinical goals. (This approach reduces the computational load by requiring a full optimization only for the base plans.)

The particular treatment plan that yields a cost-function value closest to the minimum (relative to other modeled or interpolated treatment plans) can be identified as an optimized treatment plan. Information about the optimized treatment plan can be presented to the user, e.g., in a display that includes data about dose distribution, such as a DVH for various volumes of interest and/or a color-coded image showing the dose at various points in space. In some instances, the user can iterate on the planning process, e.g., by adjusting weights in the cost function and/or by adjusting the clinical goals. Once a final optimized treatment plan is determined, adjustable machine parameters that produce the set of treatment fields corresponding to the final optimized treatment plan can be provided in machine-readable form to a radiation treatment system 100 (usually at a later time), which can be operated in accordance with the plan to deliver a radiation treatment to a patient.

3. Search Space Definition

In existing treatment planning systems that support MCO, the search space is constrained by the set of base plans (e.g., Pareto-optimal plans as described above) for which a dose prediction is computed. Additional plans within the search space can be approximated (e.g., in real time) by interpolating dose values between (or among) base plans. For instance, for a particular voxel, an interpolated dose $D'(w_1, \ldots, w_n)$ can be defined as:

$$D'(w_1, \ldots, w_n) = \sum_{i=1}^{n} w_i D_i \quad (1)$$

where $D_i$ is the predicted dose at the particular voxel for the ith base plan, n is the total number of base plans, and the weights $w_i$ are subject to the constraints that:

$$\sum_{i=1}^{n} w_i = 1 \quad (2a)$$

and, for each i:

$$0 \leq w_i \leq 1. \quad (2b)$$

A search space defined in this manner may not fully capture the possible range of machine parameter settings for a particular radiation treatment system and thus may not be a good representation of the clinically relevant tradeoffs that the radiation treatment system is physically capable of delivering.

Figure 6A:
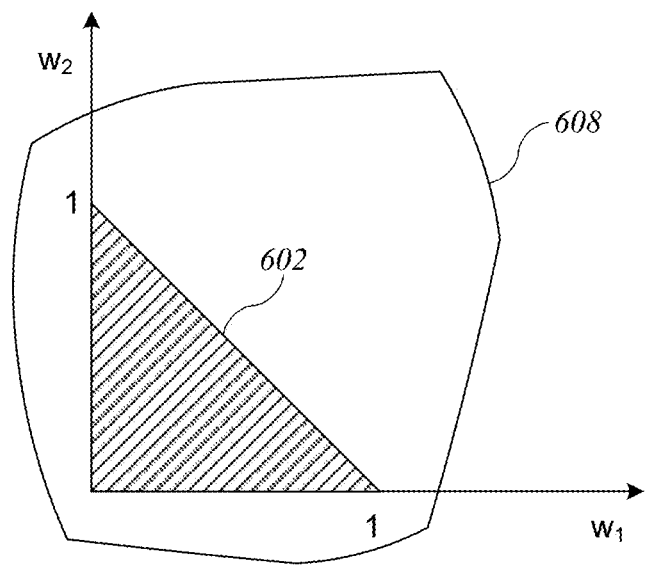
FIG. 6A shows a two-dimensional projection of a search space defined by interpolation between base plans and expanded by extrapolation.
Figure 6B:
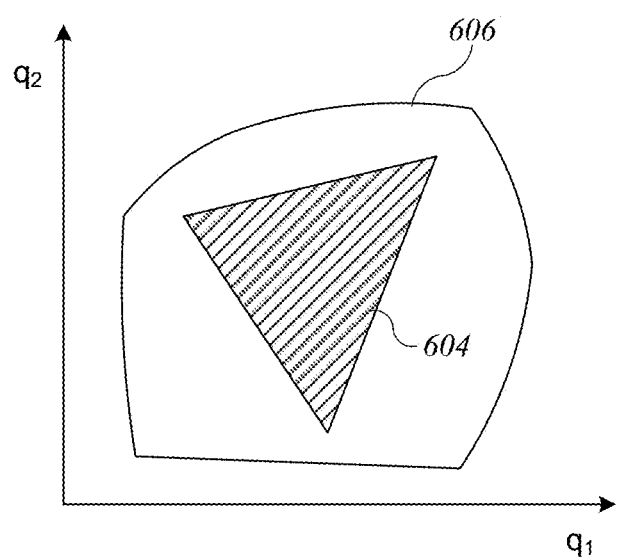
FIG. 6B shows a corresponding quality metric space.

FIGS. 6A and 6B show a simplified illustration of a limited search space. FIG. 6A shows a two-dimensional projection of a search space in the plane of weights $w_1$ and $w_2$ of two base plans. (A two-dimensional projection is shown for clarity of illustration, but the search space can have any number of dimensions.) Shaded triangle 602 corresponds to the interpolated search space defined by Eqs. (1) and (2a)-(2b). FIG. 6B shows a two-dimensional projection of a "quality metric" space in the plane of quality metrics denoted as $q_1$ and $q_2$. It is assumed in this example that quality metrics $q_j$ are defined such that $q_j$ is always nonnegative and smaller values of $q_j$ indicate better quality. For any given treatment plan, corresponding values of the quality metrics can be computed; accordingly each treatment plan maps to a point in the quality metric space. Thus, shaded triangle 604 indicates a region in quality metric space corresponding to shaded triangle 602.

4. Search Space Expansion

In the example of FIGS. 6A and 6B, interpolated search space region 602 and corresponding quality-space region 604 are not exhaustive of all combinations of machine parameter settings. In FIG. 6B, expanded boundary 606 schematically indicates the possible combinations of quality metric values for an exhaustive set of combinations of machine parameter settings. As can be seen, some possible combinations of machine parameters that are outside the search space provide better quality with respect to quality metrics $q_1$ and $q_2$ (i.e., closer to the origin) than any plans inside search region 604. FIG. 6A suggests that some of these combinations can be considered if the interpolation constraints of Eqs. (2a) and (2b) are relaxed, as indicated by expanded boundary 608. It is noted that combinations within expanded boundary 608 may provide worse quality than plans inside shaded triangle 602 with respect to quality metrics other than $q_1$ and $q_2$ (this effect is not shown in FIG. 6B), but the region within expanded boundary 608 may be of interest if the treatment planner is searching for better quality with respect to $q_1$ and $q_2$.

Accordingly, some embodiments of the present invention provide techniques for expanding the search space for MCO. In some embodiments the search space can be expanded by extrapolating from an initial set of base plans (e.g., a Pareto-optimal set of base plans) to define one or more additional "virtual" plans that can be added to the search space. Extrapolation can be performed, e.g., by applying Eq. (1) to combine base plans of the initial set while relaxing the constraints of Eq. (2a) and/or Eq. (2b). This relaxation of constraints allows the search space to expand, capturing more of the area within expanded boundary 606 of FIG. 6B, without requiring full optimization of additional treatment plans to determine dose distributions.

In some embodiments, virtual plans generated by extrapolation can be excluded subject to screening constraints. For example, referring to Eq. (1), allowing some of the weights $w_i$ to be negative may result in a negative extrapolated dose $D'$ for some voxels. For an external-beam radiation treatment system, delivering a negative radiation dose is not physically plausible. Accordingly, in some embodiments, virtual plans that produce negative dose anywhere in the modeled region can be excluded from the expanded search space. A similar constraint can also be applied with respect to fluence (beam intensity) in instances where beam intensity is modeled (e.g., for IMRT). In some embodiments, a limited number of voxels having negative doses may be permitted for a virtual plan; examples are described below.

Another type of constraint can be based on the quality metrics computed for a virtual plan. For instance, if the initial set of base plans was selected to define a Pareto-optimal surface, a virtual plan can be excluded based on its quality metrics if the virtual plan is not Pareto-optimal among the base plans or if adding the virtual plan to the set of base plans would make the initial set of base plans a non-Pareto-optimal set. As another example, if a virtual plan exceeds all of the original base plans in any quality metric, the virtual plan can be excluded as unrealistically good.

5. MCO Process with Expanded Search Space

Figure 7:
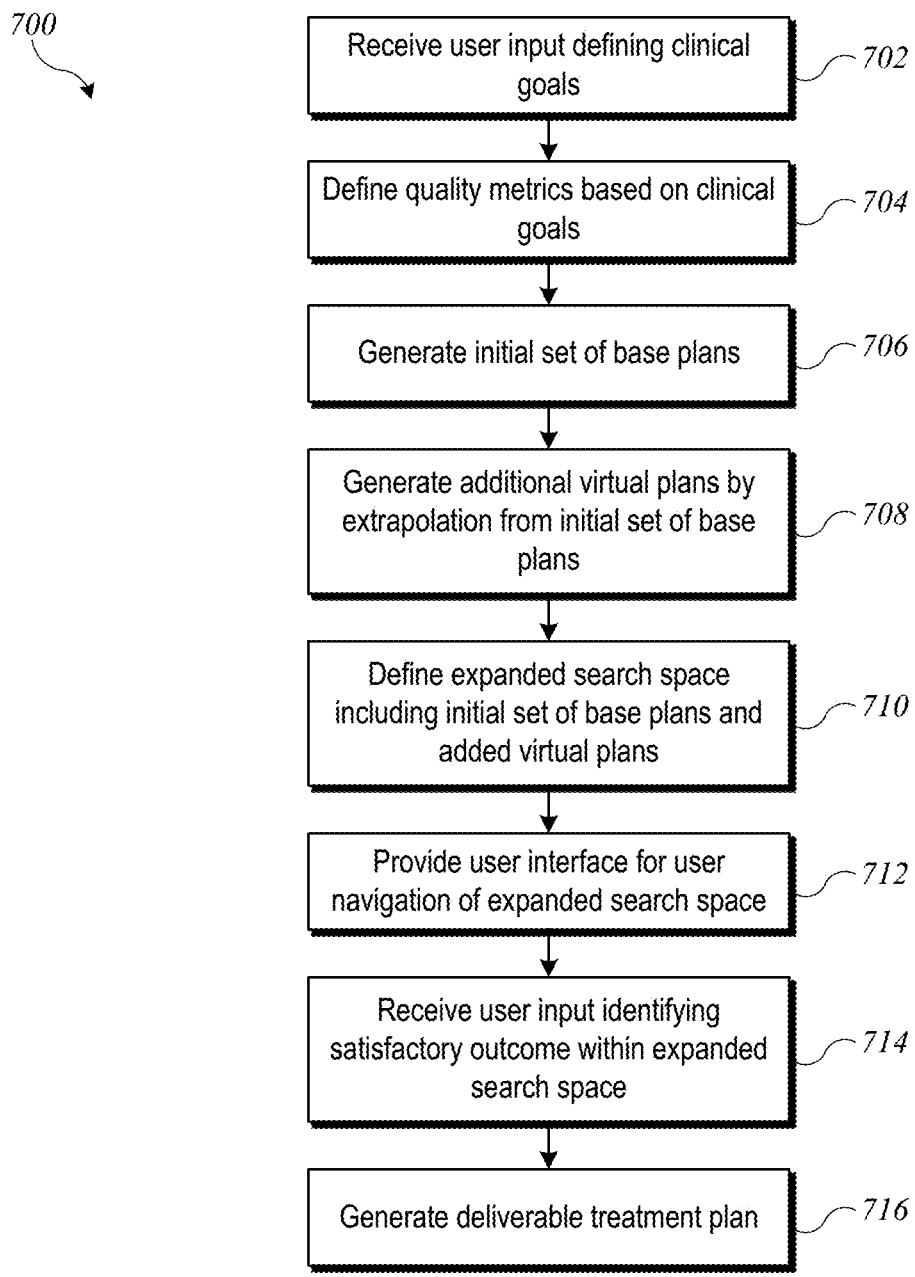
FIG. 7 is a flow diagram of a process for radiation treatment planning according to an embodiment of the present invention.

According to some embodiments of the invention, an expanded search space can be used in an interactive multi-criteria optimization (MCO) procedure for radiation treatment planning. FIG. 7 is a flow diagram of a process 700 for radiation treatment planning according to an embodiment of the present invention. Process 700 can be implemented in a computer system, e.g., using control circuitry 560 of radiation treatment system 500 (FIG. 5) or another computer system capable of providing data for use by control circuitry 560.

At block 702, process 700 can begin by receiving user input defining clinical goals for the radiation treatment. The clinical goals can include identification of a set of volumes of interest and a desired radiation dose for each. For instance, one volume of interest may be a target volume (e.g., a volume occupied by a tumor), for which a typical clinical goal is to provide at least a minimum therapeutically effective dose throughout the target volume. In some cases, there may be multiple target volumes, and each can have a different clinical goal. Other volumes of interest may correspond to different organs at risk (OARs) and/or to different portions of a single OAR, for which the treatment objective is typically to minimize the dose. In general, there are tradeoffs among these objectives, and minimizing the dose delivered to one OAR is often not possible without increasing the dose delivered to another OAR and/or reducing the dose delivered to the target volume. At block 704, a quality metric ($q_i$) corresponding to each clinical goal can be defined for purposes of optimization. For example, a quality metric can be defined to reflect a "distance" between the (predicted) outcome of a particular treatment plan and a particular clinical goal; various distance metrics can be used, and examples are known in the art. On such a definition, an ideal plan would have all quality metrics equal to zero (or the best possible value). In reality, an ideal plan is usually not physically attainable, and quality metrics can be used to facilitate finding a tradeoff plan that is physically attainable.

At block 706, process 700 can generate an initial set of "base" plans for use in the optimization procedure. Base plans can be generated by selecting a set of machine parameters and using a dose prediction model to predict the resulting dose distribution; based on the results, the parameters can be iteratively adjusted and the dose prediction updated until a particular outcome is achieved. In some embodiments, the base plans are generated by generating a Pareto-optimal set of base plans, where each base plan is optimal with respect to a different variant of a cost function that emphasizes a different one of the quality metrics. For example, a base plan that is optimal with respect to one cost function can be generated using machine parameter optimization. Specifically, a seed plan having a particular set of adjustable machine parameters (e.g., control points as described above) can be selected, and the quality metrics for the seed plan can be computed using a dose prediction model. The machine parameters can be adjusted and the effect of the adjustment on quality metrics can be computed; this process of adjusting machine parameters and determining effect on quality metrics can be iterated to converge on an optimal plan for the selected cost function. The same seed plan and iterative process can be repeated for other variants of the cost function to generate different base plans. In some embodiments, the seed plan can be a balanced plan among the quality metrics, and the seed plan can be included as an additional base plan together with the Pareto-optimal set of base plans. Accordingly, in some embodiments where the number of clinical goals is n, the initial set of base plans includes n+1 plans. Techniques for generating a set of base plans for use in MCO are known in the art, and a particular technique is not critical to understanding the present disclosure. For each base plan, the computer system 700 can store the machine parameters and the associated dose distribution.

At block 708, process 700 can generate one or more "virtual" plans by extrapolation from the initial set of base plans. As described above, extrapolation can be performed by combining base plans according to Eq. (1) using weights not subject to the constraints of Eq. (2a) and/or Eq. (2b). Any number of virtual plans may be generated.

Figure 8:
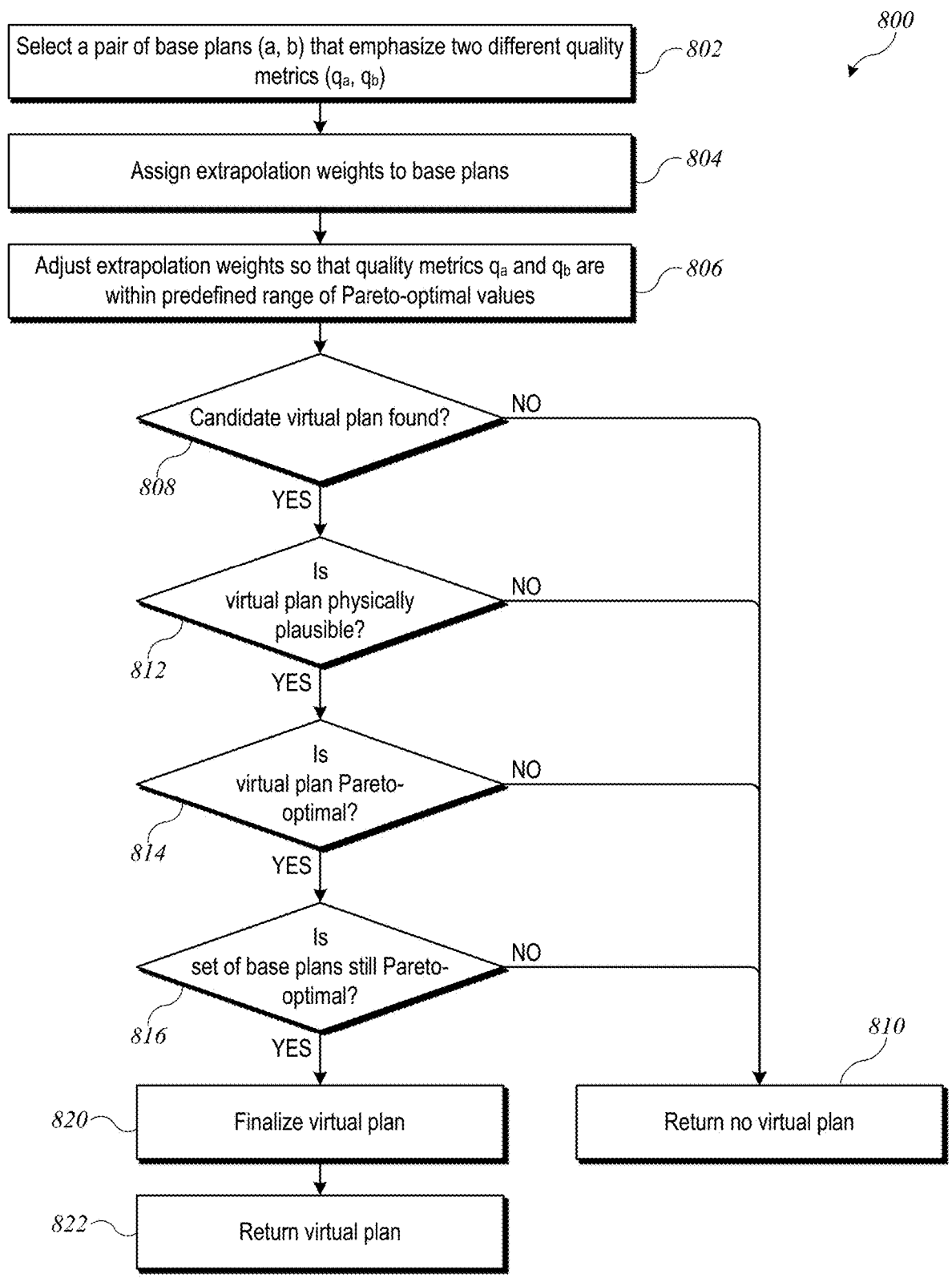
FIG. 8 shows an example of a process for generating a virtual plan using extrapolation according to an embodiment of the present invention.

FIG. 8 shows an example of a process 800 for generating a virtual plan using extrapolation according to an embodiment of the present invention. Process 800 can be used, e.g., at block 708 of process 700. Process 800 assumes that a Pareto-optimal set of base plans has already been defined.

At block 802, process 800 can select two base plans (denoted as a and b) that were generated using cost functions that emphasize two different quality metrics (denoted as $q_a$, and $q_b$, respectively). At block 804, process 800 can assign extrapolation weights ($w_i$) to each base plan in the initial set of base plans. In some embodiments, the extrapolation weights are assigned according to the following rules:

$$0.5 < w_a < 1, \quad (3a)$$

$$0.5 < w_b < 1, \quad (3b)$$

$$w_i < 0, i \neq a, b \quad (3c)$$

and $$\sum_{i=1}^{n} w_i = 1 \quad (3d)$$

A (predicted) dose distribution for the virtual plan is generated by combining the dose distributions of the base plans according to Eq. (1) using the weights assigned at block 804, and quality metrics for the virtual plan can be computed based on the predicted dose distribution and the definitions of the quality metrics from block 704 of process 700.

In some embodiments, the initial assignment of weights $w_i$ can be arbitrary (e.g., assign $w_a=w_b=0.75$, all other weights an equal negative value) so long as the constraints of Eqs. (3a)-(3d) are satisfied. At block 806, using the well-established mathematics of Pareto surfaces, the weights $w_i$ for the virtual plan can be adjusted (within the ranges given by Eqs. (3a)-(3d)) to find a combination of weights that satisfies the conditions:

$$|q_{av}-q_{a0}|<\delta \quad (4a)$$

and $$|q_{bv}-q_{b0}|<\delta \quad (4b)$$

where $q_{av}$ and $q_{bv}$ are the values of quality metrics $q_a$ and $q_b$ obtained from the virtual plan, $q_{a0}$ is the value of quality metric $q_a$ obtained from base plan a (which was generated to emphasize $q_a$ over the other quality metrics), and $q_{b0}$ is the value of quality metric $q_b$ obtained from base plan b (which was generated to emphasize $q_b$ over the other quality metrics). The limiting parameter $\delta$ can be chosen to keep the virtual plan close to the Pareto-optimal surface in quality-metric space that is defined by the base plans. A suitable value of parameter $\delta$ is a fraction of the amount of variation of the associated quality metric across the set of base plans. The result after block 806 is referred to as a "candidate" virtual plan that might be added to the search space defined by the base plans.

In some instances, for a particular pair of base plans, there may not be any set of weights that satisfies Eqs. (3a)-(3d) and (4a)-(4b). Where this is the case, at block 808, no candidate virtual plan is found, and process 800 can end at block 810 without returning a virtual plan.

Assuming a candidate virtual plan is found, additional screening criteria can be applied to determine whether to add the candidate virtual plan to the search space. For instance, at block 812, it can be determined whether the virtual plan is physically plausible. In some embodiments, a virtual plan is considered not physically plausible if it results in any voxels receiving a negative dose (or fluence), referred to as "negative voxels." Other embodiments may allow a small number of negative voxels (e.g., fewer than 1% of all voxels, fewer than 5%, fewer than 10%) or may allow negative voxels in certain regions of the modeled treatment volume (e.g., near the periphery of the irradiated region, where doses for all plans are expected to be small). Other criteria related to physical plausibility may also be applied. If it is determined that the candidate virtual plan is not physically plausible, then process 800 can end at block 810 without returning a virtual plan.

In some embodiments, it is assumed that adding virtual plans to the search space that are not part of a Pareto-optimal set is not desirable. Accordingly, at block 814, it can be determined whether the candidate virtual plan is Pareto-optimal among the base plans, e.g., whether adjusting the weights to improve one quality metric can be done without making at least one other quality metric worse. If not, then process 800 can end at block 810 without returning a virtual plan.

In some embodiments, it is assumed that virtual plans might be implausibly good Accordingly, at block 816, it can be determined whether adding the candidate virtual plan to the set of base plans would result in the base plans becoming a non-Pareto-optimal set. One example of an implausibly good virtual plan would be a virtual plan that performs better with respect to all quality metrics than any of the base plans. In some embodiments, if adding the candidate virtual plan to the set of base plans results in the base plans becoming non-Pareto-optimal, then process 800 can end at block 810 without returning a virtual plan.

It should be understood that other criteria for screening candidate virtual plans can be used in addition to or instead of those shown in FIG. 8. If all of the criteria are satisfied, then at block 820, the candidate virtual plan can be finalized for use in MCO. For instance, in embodiments where some negative voxels are allowed (at block 812), any negative voxels in a candidate virtual plan can be cropped to zero. At block 822, the process 800 can return a virtual plan and end.

Referring again to FIG. 7, it should be understood that block 708 can include multiple executions of process 800 for different pairs of base plans. In some embodiments, process 800 is performed for each pair of base plans in the initial set of base plans, with each instance of process 800 either producing a new virtual plan or not. For an initial set of n+1 base plans, this procedure can result in up to ~n² virtual plans being generated.

It should also be understood that process 800 can be modified. For instance, instead of considering pairs of base plans, the rules of Eqs. (3a)-(3d) and (4a)-(4b) can be modified and applied to triplets of plans, or to a larger subset of the base plans.

At block 710, an expanded search space is defined that includes the initial set of base plans and any virtual plans generated at block 708.

Figure 9:
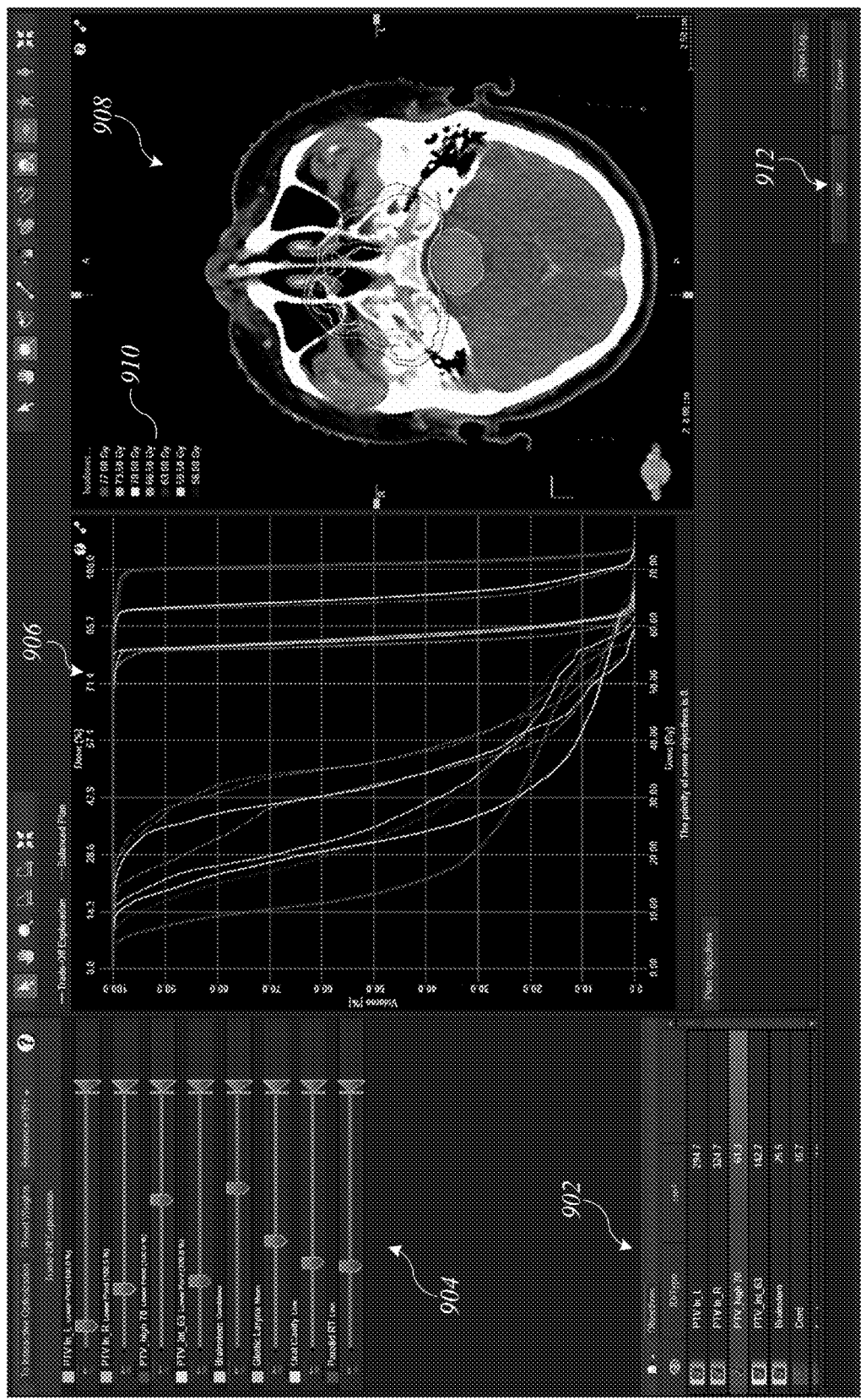
FIG. 9 shows an example of a GUI screen that can be implemented according to an embodiment of the present invention.

At block 712, a user interface is provided to facilitate user navigation of the expanded search space. For example, FIG. 9 shows an example of a GUI screen 900 that can be implemented according to an embodiment of the present invention. Regions 902 and 904 are control regions. In this example, region 902 provides a list of clinical goals. The different clinical goals can be color-coded to facilitate understanding of other information provided. Region 904 provides a separate user-operable control corresponding to each clinical goal. In this example, the controls are implemented as virtual sliders that the user can move (e.g., via a drag operation with a mouse, stylus, finger or other pointing device); other control types may be substituted. By moving the controls in region 904, the user can indicate relative importance (or weight) of different clinical goals (and consequently to the corresponding quality metric). Increasing the importance of a particular clinical goal may constrain treatment options to a particular range and may also affect the range of outcomes achievable with regard to other treatment objectives. Accordingly, when the user moves one slider, other sliders may automatically move to reflect correlations among different clinical goals.

Regions 906 and 908 provide visual feedback regarding outcomes. In some embodiments, data displayed in regions 906 and 908 is updated automatically in real time as the user moves a slider in region 904. Shown in region 906 is a dose volume histogram (DVH) for the various regions of interest (color-coded to match regions 902 and 904). Shown in region 908 is a dose distribution map for a particular slice through the patient's body. (The color coding is indicated in legend 910.) In this example, a single sagittal slice is shown. In some embodiments, GUI screen 900 may provide additional controls to allow the user to select one or more slices to view at any given time, including transverse and/or frontal slices, as well as slices at different depths. Generation of the DVH and dose distribution map may be done by interpolating dose distributions of the base plans and additional virtual plans that define the expanded search space, using interpolation weights that are generated based on the positions of the sliders. This interpolation can be done in real time, allowing for interactive operation whereby the user can adjust a slider in region 904 and view the effect in regions 906 and/or 908.

It should be understood that GUI screen 900 is illustrative. Other types of controls can be substituted, and the layout and content of various regions can be modified as desired. The selection of treatment objectives will depend on the particular goals of radiation treatment in a given case.

Referring again to FIG. 7, operation and updating of the GUI (block 712) can continue until, at block 714, user input is received indicating that the user has identified a satisfactory outcome (e.g., a satisfactory dose distribution) within the expanded search space. For instance, once a user interacting with GUI screen 900 of FIG. 9 has navigated to a combination of slider settings that provides a satisfactory dose distribution, the user may click or select "OK" button 912. "Satisfactory" in this context should be understood as meaning that the user is satisfied that: (1) the dose distribution interpolated using the current slider settings meets the goals of treatment (e.g., killing tumor cells while avoiding or limiting harm to healthy tissues); and/or (2) that further adjustment of the slider settings is not likely to lead to additional improvement.

At block 716, process 700 can generate a deliverable treatment plan based on the satisfactory outcome identified by the user. For example, for IMRT treatment planning, a deliverable treatment plan can be generated by interpolating the machine parameters of the closest base plans. For VMAT treatment planning, the base plan in the planning space whose dose distribution is closest to the satisfactory outcome identified by the user can be selected as a starting plan, and a machine parameter optimization can be performed on this starting plan using a "final" cost function formulated to produce a dose distribution similar to that of the user-defined satisfactory outcome. The optimization can be similar to the procedure for generating a base plan from a seed plan as described above.

Once the deliverable plan has been generated at block 716, process 700 can end. Thereafter, the deliverable plan can be used to control operation of radiation treatment system 100 (or radiation treatment system 500) to perform a radiation treatment on the patient. For instance, in embodiments where process 700 is implemented in control circuitry 560, control circuitry 560 can be instructed by the user to perform the radiation treatment in accordance with the deliverable plan. In embodiments where process 700 is implemented on a different computer system, the deliverable plan can be represented in a computer-readable format (e.g., a configuration file conforming to a particular syntax) and delivered to control circuitry 560 using any available file-transfer mechanism (e.g., network transfer, removable storage medium). Control circuitry 560 can read and execute the deliverable plan.

In some embodiments, the outcome selected by the user may not be the best achievable outcome. Accordingly, it may be desirable to support further optimization. For example, once a deliverable plan has been generated at block 714 of process 700, this plan may be used as a seed plan for a new round of optimization by iteratively executing process 700.

It will be appreciated that the various processes described herein are illustrative and that variations and modifications are possible. Except where internal logic requires a particular order, operations or blocks described sequentially may be executed in parallel, order of operations may be varied, and operations described in connection with different blocks can be combined. Further, it is not necessary that every operation described herein be performed in every embodiment of the invention; some operations can be omitted, and other operations not specifically described herein may be added.

6. Computer System Implementation

Figure 10:
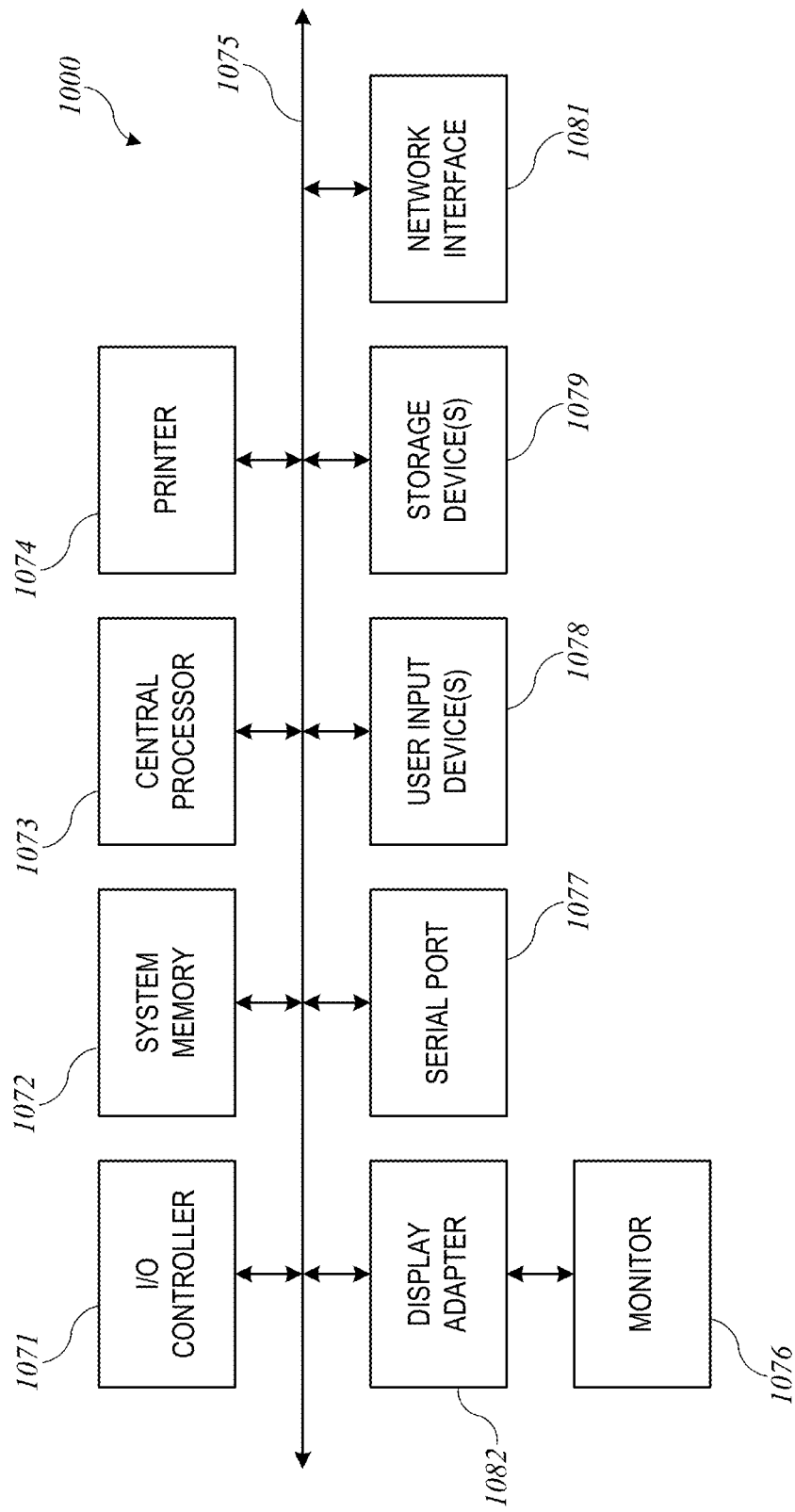
FIG. 10 shows a simplified block diagram of a computer system suitable for use in some embodiments of the present invention.

Processes described herein can be implemented in computer systems of various designs. FIG. 10 shows a simplified block diagram of a computer system 1000 suitable for use in some embodiments of the present invention. Computer system 1000 includes a number of different subsystems interconnected via a system bus 1075. The core subsystems include an input/output (I/O) controller 1071, a system memory 1072 (e.g., DRAM, SRAM, PROM, and/or other computer-readable media), and a central processor 1073. Central processor 1073, which can be implemented using one or more programmable integrated circuits (including single-core and/or multi-core microprocessors) controls operations of computer system 1000 by executing program code that can be stored (at least temporarily) in system memory 1072. Accordingly, central processor 1073 can communicate with each subsystem and can control the execution of instructions from system memory 1072 or storage device(s) 1079, as well as the exchange of information between subsystems. Similarly, any of the data mentioned herein can be delivered from one component to another component and can be output to (or input from) the user. In some embodiments, central processor 1073 may be coupled to one or more coprocessors, such as one or more graphics processing units (not shown) that are designed for high-throughput parallel processing.

I/O controller 1071 allows other components to be communicatively coupled to central processor 1073, and central processor 1073 can receive input from other components and/or send output to other components via I/O controller 1071. Accordingly, additional subsystems such as printer 1074; user input device(s) 1078 (e.g., keyboard, mouse, etc.); storage device(s) 1079 (e.g., various computer-readable media such as hard disk drives or other fixed storage devices, removable disks, removable solid-state memory devices such as USB thumb drives, etc.); monitor 1076, which is coupled to display adapter 1082; and the like may be communicably coupled to central processor 1073. Peripherals and I/O devices, which may couple to I/O controller 1071, can be connected to the computer system using various interconnect standards known in the art, such as serial port 1077. Wireless local-area connectivity (e.g., via Bluetooth or Wi-Fi or the like) may also be supported.

In some embodiments, network interface 1081 may be provided to enable communication between computer system 1000 and other computer systems, e.g., via Ethernet, Wi-Fi, or the like. Network interface 1081 may support connection to a local area network and/or to a wide-area network such as the internet. Thus, for example, processes 700 and 800 and other processes described herein can be implemented in one instance of computer system 1000, which can communicate treatment plans to another instance of computer system 1000 local to radiation treatment system 100 (e.g., including control circuitry 560).

In some embodiments, computer system 1000 is implemented as a single computer apparatus with some or all of the subsystems described above. In some embodiments, a single instance of computer system 1000 can include multiple instances of the same components or subsystems, e.g., connected together by an internal interface. In some embodiments, two or more instances of computer system 1000 (which can be configured alike or differently as desired) can communicate over a network. In such embodiments, one instance can be considered a client and another instance a server.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing or connecting electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Any of the software-implemented components or functions described in this application may be realized in the form of software code to be executed by a processor; such code may be created using any suitable computer language such as, for example, Java, C++ or Perl using, for example, conventional or object-oriented techniques. The software code may be stored as a series of instructions or commands on a computer readable storage medium; suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may also be a combination of multiple such media. Computer readable storage media encoded with the program code may be packaged with a compatible device or provided separately from other devices (e.g., as a separately packaged computer readable storage medium or via an internet download operation that results in the program code being stored on a computer readable storage medium of the device that downloaded it). Any such computer readable storage medium may reside on or within a single computer product (e.g. a hard drive, a CD, or an entire computer system) and may be present on or within different computer products within a system or network. Such programs may also be encoded and transmitted using carrier signals adapted for transmission via wired, optical, and/or wireless networks conforming to a variety of protocols, including the Internet. (It is noted that "storage" of programs or data is distinct from propagation of programs or data using transitory media such as carrier waves.)

Any of the methods described herein may be totally or partially performed with a computer system including one or more processors, which can be configured to perform the steps or operations. Thus, embodiments of the present invention can include computer systems configured to perform the steps or operations of any of the methods described herein, potentially with different components performing different steps or operations (or different groups of steps or operations).

7. Further Embodiments

While the invention has been described with reference to specific embodiments, those skilled in the art in the art with access to the present disclosure will appreciate that variations and modifications are possible and that specific embodiments described herein are intended as illustrative and not limiting. All processes described herein are illustrative, and variations and modifications are possible. Except where internal logic requires a particular order, operations or blocks described sequentially may be executed in parallel, order of operations may be varied, and operations described in connection with different blocks can be combined. Further, it is not necessary that every operation described herein be performed in every embodiment of the invention; some operations can be omitted, and other operations not specifically described herein may be added.

In embodiments described above, extrapolation from the base plans to expand the search space is performed prior to interactive user navigation. In other embodiments, extrapolation may be performed after an initial round of interactive user navigation; for instance, if the user is not satisfied with any plan generated by interpolation among the initial set of base plans, the user can input an instruction to expand the search space, at which point extrapolation is used to generate virtual plans (e.g., using process 800 of FIG. 8) prior to further user navigation. In still other embodiments, extrapolation from the base plans can be performed during interactive user navigation, e.g., by allowing extrapolation weights to be assigned in an interactive MCO solver and presenting a view of information about the resulting virtual plan.

As another example, the clinical goals described herein are generally directed toward the dose distribution for the radiation. In some cases, clinical goals not directly related to dose distribution may also be of interest in treatment planning. For example, where radiation is being delivered to a target volume in or near the lungs, it is usually advisable to have the patient hold her breath for the beam-on time (i.e., the duration of a continuous radiation exposure, such as the time required for gantry 20 to traverse a VMAT arc). Breath holding can minimize motion of the lungs or neighboring tissues, allowing radiation to be more reliably delivered to the intended target. Long breath-hold times are not always possible for a patient. Accordingly, in some embodiments of treatment planning processes as described herein, one or more additional clinical goals can be defined based on limiting the beam-on time of a treatment (e.g., traversal of a given VMAT arc) to a reasonable breath-hold time, and a user-operable control for each such clinical can be provided. In some embodiments, beam-on time for (extrapolated) virtual plans can be determined by extrapolating the beam-on times associated with the base plans using the same weights as the dose distribution. An interactive GUI screen may provide information on the beam-on time, which can be approximated by interpolation as the user navigates within the search space. Other clinical goals related to treatment time or other considerations may also be defined, and interactive optimization of such clinical goals may be supported using a GUI similar to the examples described herein.

In some embodiments described above, each treatment plan corresponds to a single continuous radiation exposure, e.g., a single IMRT exposure or a single VMAT arc traversed by the beam source. In clinical practice, a radiation therapy session may include several such treatments and may include a combination of different treatment options (e.g., one or more IMRT exposures together with one or more VMAT arcs). The processes described herein can be used to plan single-exposure treatments, and other processes can be used to plan a session including multiple single-exposure treatments. Processes described herein can be applied in the context of treatment planning for any type of radiation therapy, including electromagnetic radiation (e.g., x-rays or gamma rays), electron beams, proton beams, heavy-ion beams, and so on. Depending on the capabilities of a particular system, the treatment options can include IMRT VMAT, and/or other modulation schemes.

Thus, while the invention has been described with reference to specific embodiments, it is to be understood that the invention is defined by the following claims.

What is claimed is:

1. A method for radiation treatment planning, the method comprising:
by control circuitry:
receiving user input defining a plurality of clinical goals for a radiation treatment;
defining a plurality of quality metrics corresponding to the clinical goals;
generating an initial set of base plans, each base plan having an associated set of machine parameters and an associated dose distribution;
generating at least one virtual plan by extrapolation from the initial set of base plans, the at least one virtual plan having an associated dose distribution, wherein generating the at least one virtual plan includes:
selecting a pair of base plans from the initial set of base plans;
assigning a weight to each of the base plans in the initial set of base plans such that a positive weight is assigned to each of the selected pair of base plans and a negative weight is assigned to each other base plan in the initial set of base plans; and
computing a dose distribution for the at least one virtual plan by combining the dose distributions of the initial set of base plans according to the assigned weights;
defining an expanded search space that includes the initial set of base plans and the at least one virtual plan;
providing a user interface for navigation of the expanded search space;

receiving, via the user interface, user input identifying a satisfactory outcome within the expanded search space;

generating a deliverable treatment plan based on the user input identifying the satisfactory outcome; and operating a radiation treatment system in accordance with the deliverable treatment plan to perform a radiation treatment on a patient.

2. The method of claim 1 wherein generating the initial set of base plans includes:

generating a seed plan; and determining, from the seed plan, a Pareto-optimal set of plans, wherein each plan in the Pareto-optimal set of plans is optimized to emphasize different ones of the quality metrics, wherein the initial set of base plans includes the seed plan and the Pareto-optimal set of plans.

3. The method of claim 1 wherein generating the at least one virtual plan includes:

assigning a weight to each base plan in the initial set of base plans, wherein the weight assigned to at least one of the base plans is less than zero; and computing a dose distribution for the at least one virtual plan by combining the dose distributions of the base plans according to the weights.

4. The method of claim 1 wherein the weights are selected such that a sum of the weights is equal to 1.

5. The method of claim 1 wherein the initial set of base plans includes a Pareto-optimal set of plans, wherein each plan in the Pareto-optimal set of plans is optimized to emphasize different ones of the quality metrics, and wherein generating the at least one virtual plan further includes:

rejecting the at least one virtual plan if the at least one virtual plan is non-Pareto-optimal or renders any of the initial base plans non-Pareto-optimal.

6. The method of claim 1 wherein the at least one virtual plan is rejected if the dose distribution computed for the at least one virtual plan includes more than a maximum number of voxels having negative doses.

7. The method of claim 1 further comprising:

presenting information about the deliverable treatment plan to a user.

8. The method of claim 1 wherein the deliverable treatment plan includes a control point sequence and a multileaf collimator leaf sequence and wherein operating the radiation treatment system in accordance with the deliverable treatment plan includes:

providing, by a treatment head of the radiation treatment system coupled with a radiation source, radiation at one or more angles specified by the control point sequence and using a sequence of movements of a multileaf collimator specified by the multileaf collimator leaf sequence, such that radiation in accordance with the treatment plan is delivered to the patient.

9. A system comprising:

a memory; and a processor coupled to the memory and configured to:

receive user input defining a plurality of clinical goals for a radiation treatment;

define a plurality of quality metrics corresponding to the clinical goals;

generate an initial set of base plans, each base plan having an associated set of machine parameters and an associated dose distribution;

generate at least one virtual plan by extrapolation from the initial set of base plans and by:

selecting a pair of base plans from the initial set of base plans;

assigning a weight to each of the base plans in the initial set of base plans such that a positive weight is assigned to each of the selected pair of base plans and a negative weight is assigned to each other base plan in the initial set of base plans; and computing a dose distribution for the at least one virtual plan by combining the dose distributions of the initial set of base plans according to the assigned weights, the at least one virtual plan having an associated dose distribution;

define an expanded search space that includes the initial set of base plans and the at least one virtual plan;

provide a user interface for navigation of the expanded search space;

receive user input identifying a satisfactory outcome within the expanded search space;

generate a deliverable treatment plan based on the user input identifying the satisfactory outcome; and operate a radiation treatment system in accordance with the deliverable treatment plan to perform a radiation treatment on a patient.

10. The system of claim 9 wherein the processor is further configured such that generating the initial set of base plans includes:

generating a seed plan; and determining, from the seed plan, a Pareto-optimal set of plans, wherein each plan in the Pareto-optimal set of plans is optimized to emphasize different ones of the quality metrics, wherein the initial set of base plans includes the seed plan and the Pareto-optimal set of plans.

11. The system of claim 9 wherein the processor is further configured such that generating the at least one virtual plan includes:

assigning a weight to each base plan in the initial set of base plans, wherein the weight assigned to at least one of the base plans is less than zero; and computing a dose distribution for the at least one virtual plan by combining the dose distributions of the base plans according to the weights.

12. The system of claim 9 wherein the weights are selected such that a sum of the weights is equal to 1.

13. The system of claim 9 wherein the initial set of base plans includes a Pareto-optimal set of plans, wherein each plan in the Pareto-optimal set of plans is optimized to emphasize different ones of the quality metrics, and wherein the processor is further configured such that generating the at least one virtual plan further includes:

rejecting the at least one virtual plan if the at least one virtual plan is non-Pareto-optimal or renders any of the initial base plans non-Pareto-optimal.

14. The system of claim 9 wherein the processor is further configured such that the at least one virtual plan is rejected if the dose distribution computed for the at least one virtual plan includes more than a maximum number of voxels having negative doses.

15. The system of claim 9 wherein the processor is further configured to:

present information about the deliverable treatment plan to a user.

16. The system of claim 9 further comprising:

a treatment head coupled with a radiation source; and a multileaf collimator, wherein the processor is further configured such that operating the radiation treatment system in accordance with the deliverable treatment plan includes providing, by the treatment head, radiation from the radiation source at one or more angles specified by the treatment plan and using a sequence of movements of the multileaf collimator specified by the treatment plan, such that radiation in accordance with the deliverable treatment plan is delivered to the patient.

* * * * *